United States Patent [19]
De Haan et al.

[11] 4,136,066
[45] Jan. 23, 1979

[54] 1-CROTONYL-2,2,6-TRIMETHYLCY-CLOHEXANE

[75] Inventors: Douwe R. De Haan, Soest; Dirk K. Kettenes, Putten, both of Netherlands

[73] Assignee: P.F.W. Beheer B.V., Amersfoort, Netherlands

[21] Appl. No.: 896,224

[22] Filed: Apr. 13, 1978

Related U.S. Application Data

[60] Continuation-in-part of Ser. No. 681,202, Apr. 28, 1976, Pat. No. 4,109,022, which is a division of Ser. No. 409,099, Oct. 24, 1973, Pat. No. 3,956,392.

[30] Foreign Application Priority Data

Oct. 26, 1972 [GB] United Kingdom ............... 49368/72

[51] Int. Cl.² .............................................. C11B 9/00

[52] U.S. Cl. .................... 252/522; 260/348.57; 260/348.31 R; 260/586 C; 260/586 R; 260/586 P; 426/538; 426/590; 426/599; 568/828; 568/822

[58] Field of Search ......................................... 252/522

[56] References Cited

U.S. PATENT DOCUMENTS

| | | | |
|---|---|---|---|
| 3,822,315 | 7/1974 | Klein ............................. | 260/586 R |
| 3,956,392 | 5/1976 | De Haan et al. ................ | 260/586 R |

OTHER PUBLICATIONS

Chem. Ab. 75:151319k, 1971.

*Primary Examiner*—Veronica O'Keefe
*Attorney, Agent, or Firm*—Finnegan, Henderson, Farabow & Garrett

[57] ABSTRACT

1-Crotonoyl-2,2,6-trimethylcyclohexane occurs in four stereoisomeric forms. In particular the trans, E and cis, E isomers having interesting organoleptic properties and are useful in the preparation of perfume compositions. Processes for preparing the stereoisomers, in a pure form or as mixtures, are described.

4 Claims, 2 Drawing Figures

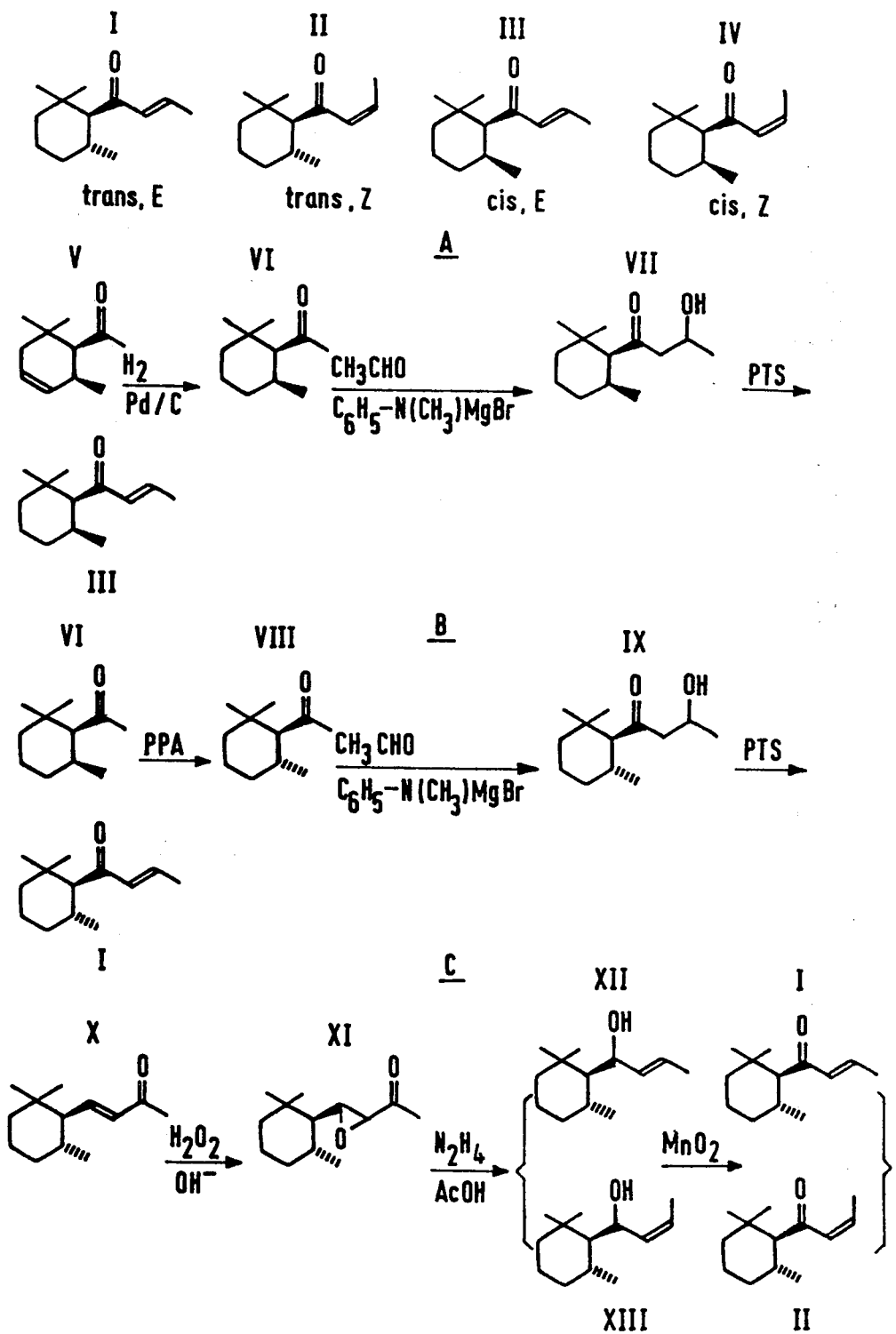

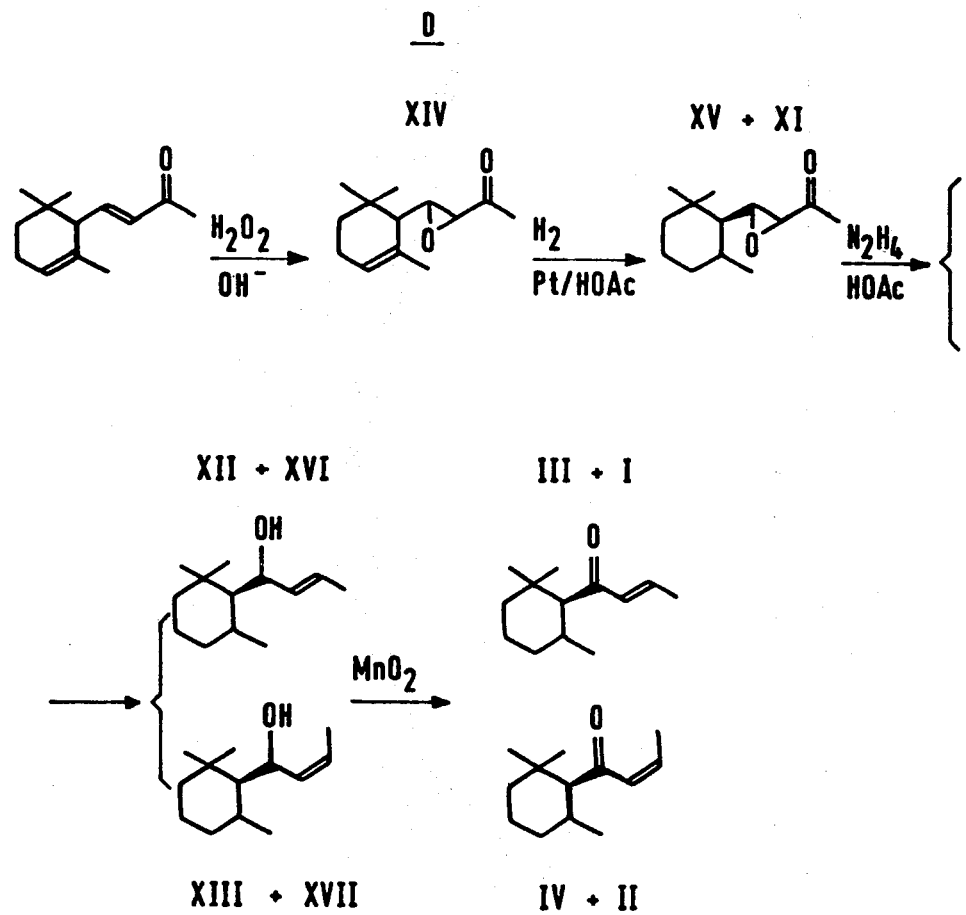

1-CROTONYL-2,2,6-TRIMETHYLCYCLOHEXANE

RELATED APPLICATION

This application is a continuation-in-part of application Ser. No. 681,202, filed Apr. 28, 1976, now U.S. Pat. No. 4,109,022, which is a division of application Ser. No. 409,099, filed Oct. 24, 1973, now U.S. Pat. No. 3,956,392.

BACKGROUND OF THE INVENTION

The present invention relates to the four stereoisomers of 1-crotonoyl-2,2,6-trimethylcyclohexane, more particularly to the trans, E and cis, E isomers, which possess unexpected interesting organoleptic properties and which therefore are useful in the preparation of a great variety of perfume compositions.

Although many examples of crotonoyl-trimethylcyclohexenes and -cyclohexadienes are knwon as flavoring and perfume materials in the recent patent literature (as are the methods of their preparation), (e.g., Dutch patent application No. 70,06649; Dutch patent application No. 68,15985; British Pat. No. 1,240,309; Swiss Pat. No. 509,399; Swiss Pat. No. 521,099; Swiss Pat. No. 521,298; E. Demole et al, Helv. Chim, Acta 53, 541 (1970), surprisingly enough there is no mention in the prior art of analogous compounds with a saturated ring system. Careful testing of the four stereoisomers has shown them to be not only totally different from the compounds with an unsaturated ring system, but also strikingly different from each other. This is less surprising than it may seem at first glance; it is known to anybody skilled in the art that the effect on the olfactive properties, as a consequence of hydrogenation of a double bond or differences in the stereo-chemistry of a molecule, cannot be predicted.

SUMMARY OF THE INVENTION

In accordance with the purpose of the invention, as embodied and broadly described herein, the perfume composition of this invention comprises a perfume base to which has been added a member selected from the group consisting of trans, E-1-crotonoyl-2,2,6-trimethylcyclohexane and cis, E-1-crotonoyl-2,2,6-trimethylcyclohexane, or mixtures thereof in an amount effective to impart a perfume characteristic to the composition. The member is preferably present in an amount of at least 0.05%, by weight, more preferably from 0.05% to 25%, and still more preferably from 0.05% to 5%.

The perfume composition may be any conventional type of perfume composition. Preferred types of perfume compositions are tuberose, mixed fruity, fancy bouquet, floral, tobacco leaf, and rose leaf perfume compositions.

This invention further comprises a method of preparing a perfume composition, which comprises adding to a perfume base an amount of a member selected from the group consisting of trans, E-1-crotonoyl-2,2,6-trimethylcyclohexane and cis, E-1-crotonoyl-2,2,6-trimethylcyclohexane, or mixtures thereof effective to impart a distinctive fragrance thereto.

BRIEF DESCRIPTION OF THE DRAWINGS

The drawings illustrate the four stereoisomers and reaction schemes for their synthesis.

DESCRIPTION OF THE PREFERRED EMBODIMENTS

The trans, E isomer is fresh fruity and devoid of any woody and β-ionone character, which as a rule is observed in crotonoyl-trimethylcyclohexenes and -cyclohexadienes. The cis, E isomer has a less fruity character but a stronger earthy-minty aspect that makes it highly useful in perfume compositions. The trans, E and cis, E isomers of the crotonoyl-trimethylcyclohexanes have been found to be superior to the latter compounds and to the trans, Z and cis, Z isomers in all perfume applications tested.

The four possible stereoisomers of the compound of this invention, represented by formulas I (trans E), II (trans Z), III (cis E), and IV (cis Z), can be prepared in a pure form or as mixtures by known per se methods.

An example of the preparation of III is the hydrogenation of cis-1-acetyl-2,2,6-trimethyl-4-cyclohexene (V). The resulting cis-1-acetyl-2,2,6-trimethylcyclohexane (VI) is condensed with acetaldehyde and the obtained aldol product VII is dehydrated to III. This synthesis can be illustrated by reaction scheme A. The hydrogenation of V can be performed in alcoholic solution with 10% palladium on charcoal as a catalyst. The resulting saturated ketone VI is then condensed with acetaldehyde under influence of N-methylanilinomagnesium bromide as described at A. T. Nielsen et al in J. Am. Chem. Soc. 73, 4696 (1951). The aldol product VII is subsequently dehydrated, in, for example, boiling methylene chloride or (azeotropically) in boiling benzene, both under the influence of p-toluenesulphonic acid to cis, E-1-crotonoyl-2,2,6-trimethyl-cyclohexane (III).

An example of the preparation of I is the epimerization of cis-1-acetyl-2,2,6-trimethylcyclohexane (VI) to the trans isomer VIII, which is condensed with actaldehyde to the aldol product IX, and then dehydrated to I. This synthesis can be illustrated by reaction scheme B. Cis-1-acetyl-2,2,6-trimethylcyclohexane (VI) can be epimerized by polyphosphoric acid at elevated temperatures. The condensation step and the dehydration are performed in the same way as described for the cis isomer III.

The starting material cis-1-acetyl-2,2,6-trimethyl-4-cyclohexene (V) can be prepared by the method described by K. S. Ayyar et al in Chem. Comm. 1973, 161 from 1,3-pentadiene and mesityl oxide in a Diels Alder-type reaction catalyzed by aluminum chloride.

An example of the preparation of a 70 : 30 mixture of I + II is the epoxidation of trans-dihydroionone (X), after which the resulting epoxide (XI) is converted by a Wharton reaction into a mixture of the unsaturated alcohols (XII and XIII), which are oxidized to a mixture of the corresponding ketones I + II. This synthesis can be illustrated by reaction scheme C. Trans-dihydroionone (X) is epoxidized at 40° C. with an alkaline solution of 30% hydrogen peroxide. The obtained epoxide (XI) is rearranged by the addition of hydrazine hydrate and acetic acid in methanolic solution at room temperature. The subsequent oxidation of the formed mixture of unsaturated alcohols XII and XIII, yielding trans, E-1-crotonoyl-2,2,6-trimethylcyclohexane (I, 70%) and trans, Z-1-crotonoyl-2,2,6-trimethylcyclohexane (II, 30%) can be performed in several ways. A satisfactory method is the oxidation with manganese dioxide in an inert solvent such as pentane. On standing II isomerizes to I. The starting material trans-dihydroionone (X) can be prepared by known methods, such as the condensation of dihydrocyclocitral with acetone under basic conditions (V. Prelog and H. Frick, Helv. Chim. Acta 31, 417 (1948); M. de Botton, Bull. Soc. Chim. France 1966, 2212, 2466).

A further example of the preparation of a mixture of all four stereoisomers is the epoxidation of α-ionone, after which the resulting epoxide XIV is hydrogenated to a mixture of dihydroionone epoxides XV and XI. These are converted by a Wharton-reaction into a mixture of the unsaturated alcohols XII, XIII, XVI and XVII, which are oxidized to a mixture of the corresponding ketones. This synthesis can be illustrated by reaction scheme D. α-ionone is epoxidized at 40° C. with an alkaline solution of 30% hydrogen peroxide. The obtained epoxide XIV is hydrogenated in acetic acid solution with platinum as the catalyst to the dihydroionone epoxides XV and XI, which are rearranged by addition of hydrazine hydrate and acetic acid in methanolic solution at room temperature. The subsequent oxidation of the formed mixture of the unsaturated alcohols XII, XIII, XVI and XVII, yielding a mixture of the four possible stereoisomers I, II, III, and IV respectively, of 1-crotonoyl-2,2,6-trimethylcyclohexane, can be performed in several ways. A satisfactory method is the oxidation with manganese dioxide in an inert solvent as for example pentane. The Z isomers II and IV have each been isolated in pure form by preparative vapor phase chromatography.

The trans, E-1-crotonoyl-2,2,6-trimethylcyclohexane possesses a powerful odor that can be described as very natural fruity, rich and warm, with an earthy-minty shading that accentuates the natural character. Its tenacity, when smelled on evaporation-blotterstrips, is very good and makes this compound of great interest for use in compositions of floral and/or woody character like iris, mimosa, boronia, tobacco, and fancy bouquets.

The cis, E isomer has a less fruity character but a stronger earthy-minty aspect that makes it highly useful in perfume compositions. Furthermore, the presence of 10-20% of cis, E isomer in the trans, E isomer results in a slightly different shade but not in a negating effect. Such a mixture can be advantageously produced according to the process of Example 6 below.

Use levels of the isomers in perfume compositions may vary within a wide range. Preferably at least 0.05% by weight of either or both is present in the final perfume, although smaller amounts can provide desirable characteristics. More preferably the final perfume contains from 0.05% to 5% of the isomers of the present invention. Perfume bases or concentrates, such as used by perfumers as ingredients in their composition work and by soap manufacturers, may contain up to 25% of the isomers of the present invention, preferably 10% to 25%. More than 25% provides no noticeable improvement and can make it difficult to provide a well-balanced composition. Thus the perfume compositions of the present invention preferably contain 0.05% to 25% of the isomer. Still more preferred are perfumes containing .05% to 5% of the trans, E or cis, E isomer in combination with other olfactorily active ingredients. In final floral perfumes the concentration of the isomers is generally lower than in compositions with a tobacco leaf or a rose leaf character, in which the level may be considerably higher than 5%.

As indicated above, the organoleptic quality of cis, E-1-crotonoyl-2,2,6-trimethylcyclohexane is quite different from that of the trans, E-isomer. The effect is far less fruity, while the earthy-minty aspect becomes dominating. The two Z isomers were found to be of far less interest for perfume purposes unless in combination with the E isomer.

The isomers disclosed and claimed herein may be added to conventional perfume bases to take advantage of their organoleptic qualities as disclosed herein. Determination of appropriate bases and concentrations of the isomers to achieve a desired effect is well within the skill of the perfume chemist using the teachings and examples of this invention as a guide to conduct routine experiments.

The isomers may be used to make final perfume compositions or to make concentrates or bases, which are later mixed with additional perfume ingredients to make a final product. The olfactorily active ingredients admixed with the isomers may control the overall character of the perfume composition while the isomer of the present invention lends a desirable, sometimes subtle, aspect.

EXAMPLE 1

Preparation of cis-1-acetyl-2,2,6-trimethylcyclohexane (VI)

464 g 1-acetyl-2,2,6-trimethyl-4-cyclohexene (V, prepared according to K. S. Ayyar Chem. Comm. 1973, 161) (2.8 moles) in 800 ml of ethanol and 3 g 10% palladium on charcoal are hydrogenated in an autoclave under a pressure of 50 atm and at 50° C. After the uptake ceases, the reaction mixture is filtered and concentrated by distillation under reduced pressure. The product cis-1-acetyl-2,2,6-trimethylcyclohexane (VI, containing about 10% of the trans isomer) is collected at 83°-88° c./12 mm; yield 420 g (90%).

EXAMPLE 2

Preparation of cis-1-(2,2,6-trimethylcyclohexyl)-3-butanolone-1 (VII)

To 750 ml of an etheral solution of ethylmagnesium bromide (prepared from 302 g (2.7 moles) of ethyl bromide and 58,7 g (2.4 moles) magnesium turnings in 550 ml of ether) is added with cooling and stirring a solution of 238 g (2.2 moles) of freshly distilled dry N-methylaniline in 700 ml of dry benzene ($N_2$ atmosphere). To the above freshly prepared solution of N-methylanilinomagnesium bromide is added during 25-30 minutes a solution of 370 g (2.2 moles) of 1-acetyl-2,2,6-trimethyl cyclohexane (VI) in 370 ml of dry benzene while keeping the temperature at 15° C. After the addition of the ketone, the solution is allowed to stand for 30 minutes. A solution of 145.5 g (3.3 moles) of freshly distilled acetaldehyde in 150 ml of dry benzene is then added during 45 minutes, keeping the temperature at −13° to −10° C. After the addition of the aldehyde, the solution is allowed to stand for 90 minutes at the same temperature. 2000 ml of 3N hydrochloric acid is then added with stirring and cooling. The organic layer is separated and washed 6 times with 1000 ml 3N hydrochloric acid (to remove the N-methylaniline) and finally with 500 ml of water, 500 ml of sodium bicarbonate solution, and then water. The combined organic layers are dried over anhydrous sodium sulfate, and the solvents are removed by distillation at reduced pressure. The residue is distilled through a short Vigreux column. The product, cis-1-(2,2,6-trimethylcyclohexyl)-3-butanolone-1 (containing about 10% of the trans isomer) is collected at 98–104° C./1 mm; yield 320 g (70%).

EXAMPLE 3

Preparation of cis, E-1-crotonoyl-2,2,6-trimethylcyclohexane (III)

A solution of 320 g (1.5 moles) of the ketol prepared in Example 2 in 1000 ml of benzene containing 2 g p-toluene-sulphonic acid is heated in an apparatus for azeotropical water separation (Dean-Stark) till no more water separates. The reaction mixture is washed with a solution of sodium bicarbonate till neutral reaction and dried over anhydrous sodium sulfate. The solvent is removed by distillation at reduced pressure and the residue is distilled through a short Vigreux column. The product, cis, E-1-crotonoyl-2,2,6-trimethyl-cyclohexane (III, contains about 10% of the trans isomer) is collected at 76° C./1 mm; yield 273 g (94%). Recrystallization from pentane gives cis, E-1-crotonoyl-2,2,6-trimethylcyclohexane in high purity (m.p. 27°–28° C.).

EXAMPLE 4

Conversion of a mixture of predominantly cis-1-acetyl-2,2,6-trimethyl cyclohexane (VI) into a mixture of predominantly the trans isomer (VIII)

A mixture of 185 g mostly cis-1-acetyl-2,2,6-trimethyl-cyclohexane (as prepared in Example 1) and 550 g of polyphosphoric acid is heated at 150° C. for about one hour. The reaction mixture is cooled to below 100° C., whereafter crushed ice is added. The mixture is extracted with benzene. The obtained extract is washed subsequently with water, a solution of sodium bicarbonate and again water, and dried over anhydrous sodium sulfate. The solvent is removed by distillation at reduced pressure, and the residue is distilled through a short Vigreux column. The product, predominantly trans-1-acetyl-2,2,6-trimethylcyclohexane, is collected at 85°–88° C./10 mm; yield 155 g (84%).

EXAMPLE 5

Preparation of trans, 1-(2,2,6-trimethylcyclohexyl)-3-butanolone-1 (IX)

By repeating the procedure described in Example 2 but replacing cis-1-acetyl-2,2,6-trimethylcyclohexane (VI) by the trans isomer VIII (as prepared in Example 4) there is obtained 67% of a mixture of the ketols IX and VII, b.p. 105°–110° C./1 mm.

EXAMPLE 6

Preparation of trans, E-1-crotonoyl-2,2,6-trimethylcyclohexane (I)

By repeating the procedure described in Example 3 but now starting from 130 g (0.61 mole) of the ketol mixture prepared in Example 5, there is obtained 99 g (84%) of a 87:13 mixture of trans, E (I) and cis, E-1-crotonoyl-2,2,6-trimethyl-cyclohexane (III), b.p. 92°–94° C./12 mm. Recrystallization from pentane gives trans, E-1-crotonoyl-2,2,6-trimethyl-cyclohexane in high purity, m.p. 8–9° C.

EXAMPLE 7

Epoxidation of trans-dihydroionone (X)

130 ml of a 30% aqueous hydrogen peroxide solution (1.1 moles) are dropped with stirring into a solution of 97 g (0.5 mole) trans-dihydroionone and 40 ml 4N sodium hydroxide solution in 500 ml of methanol. The reaction mixture is kept at 40° C. during 14 hours and then diluted with 2.5 liters of water, saturated with sodium chloride and extracted three times with 200 ml of methylene chloride. The combined organic layers are washed with water and dried over anhydrous sodium sulfate. The solvent is removed by distillation at atmospheric pressure and the residue is distilled through a short Vigreux column. The product, trans-dihydroionone epoxide is collected at 90–92° C./1 mm; yield 82 g (80%).

EXAMPLE 8

Preparation of trans, E and trans, Z-1-(2,2,6-trimethylcyclohexyl)-2-butenol-1 (XII and XIII)

In a 1-L three-necked flask fitted with a mechanical stirrer, a thermometer and a nitrogen inlet tube is placed a solution of 75 g (0.36 moles) trans-dihydroionone epoxide (XI) in 360 ml of dry methanol. Dry nitrogen is let in and within 10 minutes 53.5 g (1.0 mole) 99% hydrazine hydrate is added at a temperature of about 15° C. while cooling with ice water. Acetic acid (4.3 ml) is then added and nitrogen is evolved. The temperature is kept around 15° C. for 4 hours after which the nitrogen evolution subsides. The reaction mixture is diluted with 1 liter of water, then saturated with sodium chloride and extracted with ether. The combined organic layers are subsequently washed with water, a solution of sodium bicarbonate till neutral reaction, and again with water. The etheral solution is dried over anhydrous sodium sulfate and the solvent removed by distillation at atmospheric pressure. The residue is distilled through a short Vigreux column. The product, a mixture of trans, E and trans, Z-1-(2,2,6-trimethyl-cyclohexyl)-2-butenol-1 (XII and XIII) is collected at 80°–86° C./0.3 mm; yield 38 g (55%).

EXAMPLE 9

Oxidation of trans, E and trans, Z-1 (2,2,6-trimethylcyclohexyl)-2-butenol-1 (XII and XIII)

A solution of 7 g of the mixture of alcohols (obtained as described in Example 8), in 350 ml of dry pentane is stirred with 70 g of activated manganese dioxide during 35 hours. The course of the reaction is followed by gas chromatographic analysis. The inorganic material is removed by filtration and the solvent by distillation at atmospheric pressure. The product, 1-crotonoyl-2,2,6-trimethylcyclohexane is collected by distillation at 74° C./1 mm; yield 3.5 g (50%). The two components were separated by preparative vapor phase chromatography and found (from their IR and NMR spectra) to be the trans, Z (II) and trans, E (I) forms (30:70). On standing II isomerizes to I.

EXAMPLE 10

Epoxidation of α-ionone

A solution of 150 g (0.78 mole) of α-ionone and 80 ml of 6N sodium hydroxide solution in 865 ml of methanol is brought to 35° C. 282 ml of a 35% aqueous hydrogen peroxide solution (2.9 moles) are added with stirring during 45 minutes. The reaction mixture is kept at 35°–40° C. during 4 hours and then concentrated to 500 ml. The residue is diluted with 300 ml of water, saturated with sodium chloride and extracted three times with 200 ml of chloroform. The combined organic layers are washed with water and dried over anhydrous sodium sulfate. The solvent is removed by distillation at reduced pressure, and the residue is distilled through a short Vigreux column. The product, α-ionone epoxide (XIV), is collected at 98–102° C./1 mm; yield 114 g (70%).

EXAMPLE 11

Hydrogenation of α-ionone epoxide (XIV)

A solution of 130 g α-ionone epoxide (XIV) (0.62 mole) in 300 ml of glacial acetic acid is hydrogenated in a Parr hydrogenation apparatus with 1 g platinum oxide as a catalyst under a pressure of 50 p.s.i. till the uptake ceases. The small amount of dihydroionol epoxide which is also formed, is reoxidized by adding enough chromic acid solution in water at 25–35° C. to create a persistent orange-red color for one hour. The reaction mixture is diluted with 1 liter of water, then extracted three times with pentane. The combined organic layers are washed with water and a solution of sodium bicarbonate till neutral reaction and dried over anhydrous sodium sulfate. The solvent is removed by distillation at reduced pressure and the residue is distilled through a short Vigreux column. The product, consisting of cis (90%) (XV) and trans (10%) (XI) dihydroionone epoxide is collected at 96–97° C./1 mm; yield 95 g (70%).

EXAMPLE 12

Preparation of 1-(2,2,6-trimethylcyclohexyl)-2-butenol-1

The same procedure as is described in Example 8 is applied to 90 g (0.42 mole) of the mixture of cis- and trans-dihydroionone epoxide, as obtained in Example 11. The product, a mixture of all four stereoisomers of 1-(2,2,6-trimethylcyclohexyl)-2butenol-1 is collected at 92–96° C./1 mm; yield 33 g (40%).

EXAMPLE 13

Oxidation of the mixture of alcohols from Example 12

The same procedure as is described in Example 9 is applied to 25 g (0.13 mole) of the mixture of alcohols obtained in Example 12. The product, a mixture of all four stereoisomers of 1-crotonoyl-2,2,6-trimethylcyclohexane (III:IV:I:II in a ratio of 60:27:9:4) is collected by distillation at 80–90° C./1 mm; yield 13 g (50%). cis, Z (IV) is isolated from the foregoing mixture by preparative vapor phase chromatography.

EXAMPLE 14

A perfume composition concentrate or base, suitable for admixture with other perfume ingredients, was prepared by mixing together the following ingredients (parts by weight):

| | |
|---|---|
| 250 | δ-undecalactone |
| 100 | dihydrojasmone |
| 50 | methyl 2-n-hexyl-3-oxo-cyclopentanecarboxylate (PFW) |
| 100 | allyl heptanoate |
| 50 | eugenol |
| 50 | geranyl acetate |
| 50 | dimethylbenzylcarbinyl butyrate |
| 5 | isocyclocitral |
| 15 | cis-3-hexenyl acetate (10% solution in diethylphthalate) |
| 15 | cis-3-hexenol (10% solution in diethylphthalate) |
| 5 | methyl ethylphenylglycidate |
| 60 | linalyl isobutyrate |
| 250 | cis-E-1-crotonoyl-2,2,6-trimethylcyclohexane |
| 1000 | |

This composition has a very strong mixed fruity character: apple, prune, apricot-gooseberry, in which the cis-E isomer of 1-crotonoyl-2,2,6-trimethylcyclohexane plays a dominant role.

EXAMPLE 15

A perfume composition concentrate or base, suitable for admixture with other perfume ingredients, was prepared by mixing together the following ingredients:

| | |
|---|---|
| 10 | methyl octinecarboxylate |
| 50 | heliotropine |
| 200 | hydroxycitronellal |
| 200 | linalool |
| 100 | Ylang-Ylang premier |
| 10 | δ-dodecalactone |
| 100 | Schiff's base of 4-(4-methyl-4-hydroxypentyl)-3-cyclohexenecarboxaldehyde (IFF) with methyl anthranilate |
| 10 | methyl anthranilate |
| 10 | 4-(p-hydroxyphenyl)-butanone-2 (IFF) |
| 10 | 8,8-di(3H-indolyl-3)-2,6-dimethyl-2-octanol (Roure Bertrand) |
| 25 | cis-3-hexenyl benzoate |
| 25 | cis-3-hexenyl salicylate |
| 250 | trans-E-1-crotonyl-2,2,6-trimethylcyclohexane |
| 1000 | |

This composition has a strong tuberose character with a very long lasting dry-out. The trans-E-isomer of 1-crotonoyl-2,2,6-trimethylcyclohexane is one of the pushing factors.

EXAMPLE 16

A perfume composition of the fancy bouquet type was prepared by mixing together the following ingredients (in parts by weight):

| | |
|---|---|
| alpha-methyl ionone | 300 |
| isoeugenol | 10 |
| coumarin | 30 |
| hydroxycitronellal | 150 |
| linalool | 150 |
| linalyl acetate | 80 |
| Vetivert oil | 20 |
| benzyl acetate | 60 |
| phenylethyl alcohol | 30 |
| geraniol | 50 |
| bergamot oil | 50 |
| heliotropin | 10 |
| anisaldehyde | 5 |
| benzyl salicylate | 55 |
| | 1000 |

To aliquotes of this basic composition was added: (a) 10 parts of cis, E 1-crotonoyl-2,2,6-trimethylcyclohexane; (b) 10 parts of the same containing 10% of the trans E isomer.

The composition obtained after addition of either (a) or (b) showed a definite perfumistic improvement (more impact, more unity, and more characteristic). The presence of the trans E isomer in the cis, E isomer to an extent of 10% is neither beneficial nor has it a negating effect in this particular example.

It will be apparent to those skilled in the art that various modifications and variations could be made in the perfume compositions of the invention without departing from the scope or spirit of the invention.

What is claimed is:

1. A perfume composition to which has been added a member selected from the group consisting of trans, E-1-crotonoyl-2,2,6-trimethylcyclohexane and cis, E-1-crotonoyl-2,2,6-trimethylcyclohexane, or mixtures thereof in an amount effective to impart a perfume characteristic to said composition.

2. A perfume composition according to claim 1, wherein said member is the trans, E isomer.

3. A perfume composition according to claim 1, wherein said member is the cis, E isomer.

4. A method of preparing a perfume composition, which comprises adding to a perfume base an amount of a member selected from the group consisting of trans, E-1-crotonoyl-2,2,6-trimethylcyclcohexane and cis, E-1-crotonoyl-2,2,6-trimethylcyclohexane, or mixtures thereof effective to impart a distinctive fragrance thereto.

* * * * *